United States Patent [19]

Russell et al.

[11] Patent Number: 5,411,973
[45] Date of Patent: May 2, 1995

[54] THERAPEUTIC ALCOHOLS

[75] Inventors: Keith Russell, Newark; James R. Empfield, Bear; Cyrus J. Ohnmacht, Wilmington, all of Del.; Keith H. Gibson, Prestbury, England

[73] Assignee: Zeneca Limited, England

[21] Appl. No.: 63,373

[22] Filed: May 18, 1993

[30] Foreign Application Priority Data

May 18, 1992 [GB] United Kingdom ............ 9210577
Jan. 25, 1993 [GB] United Kingdom ............ 9301438

[51] Int. Cl.$^6$ .............. C07C 49/835; C07C 317/22; C07D 213/50; A61K 31/10
[52] U.S. Cl. ............... 514/347; 514/354; 514/385; 514/646; 514/648; 514/687; 514/710; 514/711; 568/29; 568/32; 568/33; 568/333; 564/328; 564/430; 546/294; 546/314; 546/315; 546/328; 544/316; 544/318; 544/335
[58] Field of Search ............. 568/33, 29, 333, 32; 546/294, 315, 314, 328; 564/328, 430; 514/710, 711, 648, 646, 687, 354, 355, 347; 544/316, 318, 335

[56] References Cited

U.S. PATENT DOCUMENTS

| | | | |
|---|---|---|---|
| 3,291,837 | 12/1966 | Goldberg et al. | 260/591 |
| 3,998,890 | 12/1976 | Karrer et al. | 260/609 F |
| 4,845,119 | 7/1989 | Hughes et al. | 514/450 |
| 4,873,329 | 10/1989 | Hughes et al. | 544/265 |
| 5,032,592 | 7/1991 | Hughes et al. | 514/256 |

FOREIGN PATENT DOCUMENTS

| | | |
|---|---|---|
| 2020971 | 1/1991 | Canada . |
| 0181568A2 | 5/1986 | European Pat. Off. . |
| 0189142A2 | 7/1986 | European Pat. Off. . |
| 0409413A2 | 1/1991 | European Pat. Off. . |
| 0524781A1 | 1/1993 | European Pat. Off. . |
| 2238044 | 3/1991 | United Kingdom . |

OTHER PUBLICATIONS

R. Bayles, et al. "The Smiles Rearrangement of 2-Aryloxy-2-methylpropanamides. Synthesis of N-Aryl-2-hydroxy-2-methylpropanamides" *Synthesis* (1977), (1), 31–33.

B. Delfort, et al. "Ethynyl-Terminated Polyethers from New End-Capping Agents: Synthesis and Characterization" *Journal of Polymer Science: Part A: Polymer Chemistry* (1990), 28 (9), 2451–2464.

G. Edwards, A. Weston "Structure-activity Relationships of K+ Channel Openers" *Trends in Pharmacological Sciences* (1990), 11 (10), 417–422.

J. J. Morris, et al. "Non-Steroidal Antiandrogens. Design of Novel Compounds Based on an Infrared Study of the Dominant Conformations and Hydrogen-Bonding Properties of a Series of Anilide Antiandrogens" *J. Med. Chem.* (1991), 34, 447–455.

Pinder et al, "Trifluoromethyl Analogs of Amphetamine and Norephedrine", Journal Pharmaceutical Sciences vol. 56, No. 8, (1967), pp. 970–973.

*Primary Examiner*—Johann Richter
*Assistant Examiner*—John Peabody
*Attorney, Agent, or Firm*—Cushman Darby & Cushman

[57] ABSTRACT

Compounds of formula I

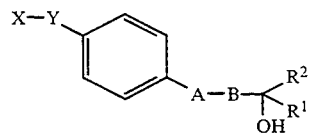

wherein X, A, B, $R^1$ and $R^2$ have the meanings given in the specification, and pharmaceutically acceptable salts and pharmaceutically acceptable in vivo hydrolysable ester thereof, processes for preparing the compounds and pharmaceutical compositions comprising them. The compounds are useful as potassium channel openers and as therapeutic agents in the treatment of urinary incontinence.

7 Claims, No Drawings

THERAPEUTIC ALCOHOLS

This invention relates to compounds useful as cell potassium channel openers in mammals such as man. More specifically, the invention relates to certain substituted alcohols which are useful in the treatment of urinary incontinence in mammals. Because compounds according to the invention function to open cell potassium channels, they may also be useful as therapeutic agents in the treatment of conditions or diseases in which the action of a therapeutic agent which opens potassium channels is desired or is known to provide amelioration. Such conditions or diseases include hypertension, asthma, peripheral vascular disease, right heart failure, congestive heart failure, angina, ischemic heart disease, cerebrovascular disease, renal cholic, glaucoma, disorders associated with kidney stones, irritable bowel syndrome, male pattern baldness, premature labor, impotence, and peptic ulcers.

Treatment using a compound of the invention can be remedial or therapeutic as by administering a compound following the onset or development of urinary incontinence in a patient. Treatment can also be prophylactic or prospective by administering a compound in anticipation that urinary incontinence may develop, for example in a patient who has suffered from incontinence in the past.

It is known that bladder tissue is excitable and that urinary incontinence can be caused by uncontrolled or unstable bladder contractions. It is further known that by functioning to open potassium channels, potassium channel opening compounds can thereby function to relax smooth muscle. While not wishing to be bound by theory, it is accordingly believed that the compounds of this invention function by opening potassium channels in bladder cells and thereby relax or stabilize bladder smooth muscle tissue, thus preventing or ameliorating uncontrolled bladder contractions which can cause urinary incontinence.

European patent applications publication numbers 0181568 and 189142 disclose large groups of compounds which are said to be lipoxygenase inhibitors and to possess anti-inflammatory and anti-allergic properties. These specifications make no suggestion of compounds having any activity as potassium channel openers.

This invention provides a tertiary carbinol having formula I (formula set out, together with other formulae referred to in the specification by Roman numerals, on pages following the Examples), wherein:

X is selected from
  (a) phenyl which may bear 0–2 substituents selected from fluoro, chloro, and hydroxy,
  (b) 2-pyridyl, 3-pyridyl, 4-pyridyl, and 2-pyrimidinyl;

Y is selected from sulfonyl or carbonyl;

A–B is selected from $OCH_2$, $SCH_2$, $NHCH_2$, trans-vinylene, and ethynylene;

$R^1$ and $R^2$ are independently selected from the group consisting of methyl, monofluoromethyl, difluoromethyl, trifluoromethyl, ethyl and pentafluoroethyl, provided that at least one of $R^1$ and $R^2$ is fluorine-bearing;

or a pharmaceutically acceptable in vivo hydrolyzable ester or a pharmaceutically acceptable salt thereof.

The invention further provides a method for the treatment of urinary incontinence, comprising administering to a mammal (including man) in need of such treatment an effective amount of an alcohol of formula I as defined above, or a pharmaceutically acceptable in vivo hydrolyzable ester or pharmaceutically acceptable salt thereof.

The invention further provides a pharmaceutical composition suitable for the treatment of urinary incontinence comprising an alcohol of formula I as defined above, or a pharmaceutically acceptable in vivo hydrolyzable ester or pharmaceutically acceptable salt thereof, and a pharmaceutically acceptable diluent or carrier.

It will be appreciated by those skilled in the art that certain compounds of formula I contain an asymmetrically substituted carbon, and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the treatment of urinary incontinence, it being well known in the art how to prepare optically-active forms (for example, by resolution of the racemic form, by synthesis from optically-active starting materials, by chiral synthesis, or by chromatographic separation using a chiral stationary phase) and how to determine efficacy for the treatment of urinary incontinence by the standard tests described hereinafter. It may be preferred to use the compound of formula I in a form which is characterized as containing, for example, at least 95%, 98% or 99% enantiomeric excess (ee).

Particular values of phenyl substituted with 0–2 substitutents include phenyl, 2-, 3-, and 4-hydroxyphenyl, 2-, 3-, and 4-fluorophenyl, 2-, 3- and 4-chlorophenyl, 2,4-difluorophenyl, 2,3-difluorophenyl, 3,5-difluorophenyl, 2,4-chlorophenyl, 2,3-chlorophenyl, 3,5-dichlorophenyl, 2,4-dihydroxyphenyl, 2,3-dihydroxyphenyl, and 3,5-dihydroxyphenyl.

Particular values of $R^2$ include:
  trifluoromethyl when $R^1$ is methyl, monofluoromethyl, trifluoromethyl, ethyl, or pentafluoroethyl;
  difluoromethyl when $R^1$ is difluoromethyl;
  methyl, ethyl, pentafluoroethyl, or trifluoromethyl when $R^1$ is pentafluoroethyl.

Preferred compounds are those in which $R^1$ and $R^2$ are each difluoromethyl or $R^2$ is trifluoromethyl and $R^1$ is methyl or monofluoromethyl. Such compounds have been found to exhibit particularly good potency as bladder smooth muscle relaxants.

More particular values of phenyl substituted with 0–2 substitutents include those values of phenyl substituted with 0–1 substituent, including phenyl, 2- and 3-hydroxyphenyl, 2- and 3-fluorophenyl, and 2- and 3-chlorophenyl.

Preferably X is phenyl, 2-pyridyl or 4-pyridyl.

More particular values of the group A–B include $OCH_2$, trans-vinylene, and ethynylene.

Preferred compounds include: 4,4,4-trifluoro-3-hydroxy-3-methyl-1-(4-phenylsulfonylphenyl)-trans-but-1-ene; (S)-(-)-4,4,4-trifluoro-3-hydroxy-3-methyl-1-(4-phenylsulphonylphenyl)-trans-but-1-ene;
  4,4,4-trifluoro-3-hydroxy-3-methyl-1-(4-phenylsulphonylphenyl)but-1-yne;
  4,4-difluoro-3-difluoromethyl-3-hydroxy-1-(4-phenylsulfonylphenyl)-but1-yne.; and
  4,4-difluoro-3-difluoromethyl-3-hydroxy-1-(4-phenylsulphonylphenyl) trans-but-1-ene.

A tertiary carbinol of formula I can be made by processes which include processes known in the chemical arts for the production of structurally analogous compounds. Such processes for the manufacture of a carbinol of formula I as defined above are provided as further features of the invention and are illustrated by the following procedures in which the meanings of generic radicals are as given above unless otherwise qualified. Such a process can be effected, generally, (a) by deprotecting a corresponding compound of formula II, wherein Pr is a protective group such as aryl- or lower alkylcarbonyl (the protecting linkage thereby constituting an ester) or trialkylsilyl (for example trimethylsilyl), by treatment with an appropriate deprotective agent, for example tetrabutylammonium fluoride (TBAF) in THF if the group Pr is a silyl group, or potassium (or other alkali metal) carbonate in methanol if the group OPr is an ester. The reaction can generally be conducted from about room temperature to about reflux.

(b) when Y is carbonyl
(i) by deprotecting a corresponding compound of formula III, for example by treating it with a saturated aqueous acid such as oxalic or a mineral acid such as hydrochloric acid or sulphuric acid. The reaction can be conducted at a temperature of from about 0° to about 100° C. in a solvent such as a lower alcohol (e.g., methanol or ethanol), or mixtures of solvent pairs such as water/dichloromethane, water/THF, and water/acetone.

(ii) by treating a corresponding compound of formula IV, wherein $G^1$ is a leaving group such as bromo or iodo, with a tin compound having the formula $SnX_4$ ("X " having been previously defined) and carbon monoxide to effect carbonylative coupling, in the presence of a suitable carbonylation catalyst such as bis(triphenylphosphine)palladium dichloride. The reaction can be conducted at a temperature of about 0° to about 100 ° C. and in a solvent such as THF, DMPU, or DMSO.

(iii) by treating a corresponding compound of formula IV with an aluminum compound having the formula $AlX_3$ and carbon monoxide to effect carbonylative coupling, in the presence of a suitable carbonylation catalyst such as bis(triphenylphosphine)palladium dichloride. The reaction can be conducted at a temperature of about 0° to about 100 ° C. and in a solvent such as diethyl ether, benzene, toluene, or THF.

(c) when Y is sulfonyl and A-B is vinylene or ethynylene, by treating a corresponding compound of formula V with a compound of formula $R^2M$ wherein M is an alkali metal (such as lithium) or a Grignard compound of formula $R^2MgBr$ or $R^2MgCl$. The reaction can be conducted at a temperature of about −100° to about 0° C. and in a solvent such as THF, diethyl ether, or DME.

(d) when A-B is ethynylene, by coupling a corresponding compound of formula VII, wherein G is a leaving group such as bromo, iodo, or triflate, with a corresponding acetylene of formula VIII, in the presence of a suitable catalyst such as a combination of cuprous iodide and bis(triphenyl-phosphine)palladium dichloride or palladium(II) acetate. The reaction can be conducted in an inert solvent such as THF, benzene, or toluene, or in a basic solvent such as diethylamine (DEA) or triethylamine (TEA), and at a temperature in the range of −20° to 110° C.

(e) when A-B is ethynylene, by reacting a corresponding ethynylbenzene of formula IX with a base such as lithium diisopropylamide (LDA), n-butyllithium or tert-butyllithium, followed by treatment with a ketone of formula $R^1$—CO—$R^2$. The reaction can be conducted at a temperature of from about −100° to about −40° C. and in a solvent such as tetrahydrofuran (THF), diethyl ether, or 1,2-dimethoxyethane (DME).

(f) when A-B is trans-vinylene,
(i) by reducing a corresponding acetylene of formula XI with a suitable reducing agent, for example lithium aluminum hydride or sodium bis(2-methoxyethoxy)aluminium hydride. The reaction can be conducted in a suitable solvent such as THF, diethyl ether or toluene, and at a temperature of about 0° to about 50° C.

(ii) by treating a corresponding trans-vinylene compound of formula XII with an organolithium compound of formula $R^1Li$. The reaction can be conducted at a temperature of from about −100° to about 25° C. and in a solvent such as THF, diethyl ether, or DME.

(iii) dehydration of a diol of formula XXXV in the presence of an acid catalyst (for example p-toluenesulfonic acid), neat or with a solvent such as toluene or dichloromethane, and at a temperature of about 0° to about 200° C.

(g) when Y is sulfonyl, by treating a corresponding compound of formula IV wherein G is a leaving group such as bromo or iodo with a compound of formula $XSO_2^+Na^+$ in the presence of a suitable catalyst such as cuprous oxide. The reaction can be conducted at a temperature of from about 30° to about 200° C. and in a solvent such as DMF, DMPU, DMSO, or ethylene glycol.

(h) when A-B is other than $SCH_2$ and Y is sulfonyl, by oxidizing a sulfide of formula XIV with a suitable oxidizing agent/solvent/temperature combination such as (i) sodium periodate in methanol or dioxane at a temperature in the range of about 20° to about 80° C.; (ii) 30% hydrogen peroxide in glacial acetic acid at a temperature of from about 20° to about 70° C.; (iii) potassium permanganate in a combination of acetic acid and water at about room temperature; (iv) oxone in a combination of water and methanol at about room temperature; (v) m-chloroperoxybenzoic acid (mCPBA) in methylene dichloride at a temperature of from about 0° C. to reflux.

(i) when A-B is $NHCH_2$, by reducing an amide of formula XV with a suitable reducing agent such as lithium aluminum hydride or borane. The reaction can conveniently be conducted at a temperature of from about 0° C. to about reflux solvents such as for example diethyl ether, THF, or DME.

(j) when A-B is $OCH_2$ or $SCH_2$, by reacting an ethylene oxide of formula XVI with a phenol or thiophenol of formula XVII (wherein J is, correspondingly, oxygen or sulfur), in the presence of a base such as sodium hydride. The reaction can be conducted at reflux in a solvent such as methylene dichloride. The ethylene oxide may conveniently be prepared in situ from a corresponding ketone of formula $R^1COR^2$ as described in Examples 1-3.

(k) when A-B is $OCH_2$, $SCH_2$, or $NHCH_2$, by heating, in the presence of a base such as an alkali metal hydride and at a temperature from about 20° C. to about reflux, a corresponding compound of formula XVIII, wherein $R^4$ is OH, SH, or $NH_2$, in a solvent such as DMF, thereby effecting rearrangement to a corresponding compound of formula I.

(1) when A-B is $OCH_2$, $SCH_2$, or $NHCH_2$, by treating a corresponding phenol, thiophenol, or aniline (wherein J is, correspondingly, oxygen, sulfur, or NH) of formula XVII with a triflate of formula XIX, wherein Pr is a protective group such as silyl, in the presence of a base such as an alkali metal hydride (e.g., sodium hydride), in a solvent such as THF, DMF, DMSO, or DMPU, and at a temperature of about 20° C. to about reflux, followed by deprotection by treating the reaction product with a deprotecting agent (e.g., tetrabutylammonium fluoride in THF if silyl is the protecting group).

(m) when A-B is trans-vinylene, by base catalyzed opening of an epoxide of formula XXXII. The opening may be carried out in a suitable organic solvent such as for example, ethers, alcohols, or toluene; ethers such as tetrahydrofuran are preferred. Suitable bases include for example sodium hydroxide, sodium methoxide, potassium tert-butoxide or sodium hydride. A basic aqueous solution may conveniently be employed. A preferred base is aqueous sodium hydroxide. The opening may be carried out at a temperature in the range of −50° C. to 100° C., preferably at a temperature in the range of 0° to 50° C., such as for example room temperature. The opening may conveniently be carried out under conditions similar to those described in Example 13.

(n) when A-B is trans-vinylene, by dehydration of a diol of formula XXXI using a suitable base. The dehydration may be carried out in a suitable organic solvent, for example, ethers such as tetrahydrofuran. The dehydration may be carried out at a temperature in the range of −78° C. to 100° C., preferably at a temperature in the range of 0° to 50° C., such as for example room temperature. The dehydration may conveniently be carried out under conditions similar to those described in Example 14 and 13(e).

(o) when Y is sulfonyl, A-B is vinylene or ethynylene, and $R^1=R^2$; by treating a corresponding compound of formula VI with a compound of formula $R^1M$ wherein M is an alkali metal (such as lithium) or a Grignard compound of formula $R^1MgBr$ or $R^1MgCl$. The reaction can be conducted at a temperature of about −100° to about 0° C. in a suitable solvents such as for example THF, diethyl ether, or DME.

If not commercially available, the necessary starting materials for the procedures such as that described above may be made by procedures which are selected from standard organic chemical techniques, techniques which are analogous to the synthesis of known, structurally similar compounds, or techniques which are analogous to the above described procedure or the procedures described in the examples.

A compound of formula II can be made by protecting a corresponding alcohol made in essentially any earlier stage of synthesis, for example an alcohol of formula IV, VIII, XI, XIV, XV, or XXII. The alcohol can be treated with a compound which reacts to form a trialkylsilyl (e.g. trimethylsilyl) group, such as trimethylsilyl chloride or trimethylsilyl triflate, in the presence of a base such as sodium hydride, diisopropylethylamine or triethylamine. A preferred base is diisopropylethylamine. Alternatively, if an ester protecting group is desired the alcohol can be reacted with an acid chloride of formula R5COCl or an acid anhydride of formula $(R^5CO)_2O$ wherein $R^5$ is a lower alkyl or aryl group. The reaction can be conducted in a solvent such as dichloromethane, in the presence of a base such as TEA and dimethylaminopyridine (DMAP), and at a temperature of −40° to about 25° C.

A compound of formula III, wherein A-B is ethynylene, can be made by reacting a corresponding compound of formula XX with a base such as an alkyllithium (for example, butyllithium) followed by addition of a ketone having the formula $R^1$—CO—$R^2$ The reaction can be conducted at a temperature of from about −100° to about −40° C. and in a solvent such as THF, dimethyl ether, or DME.

A compound of formula III, wherein A-B is trans-vinylene, can be made by reducing a corresponding compound of formula III, wherein A-B is ethynylene, with a suitable reducing agent such as lithium aluminum hydride or sodium bis(2-methoxyethoxy)aluminum, in a solvent such as THF and at room temperature.

A compound of formula XX can be made by treating a corresponding compound of formula XXI with 1,3-propanediol in the presence of an acid catalyst such as p-toluenesulfonic acid (TsOH) and in a refluxing solvent such as toluene.

A compound of formula XXI can be made by (1) treating a compound of formula VII wherein Y is carbonyl and G is bromo with a protected acetylene such as trimethylsilylacetylene in the presence of a catalyst such as a combination of cuprous iodide and bis(triphenylphosphine)palladium dichloride in a solvent such as diethylamine, thereby making a corresponding compound of formula XXIa, followed by (2) removal of the silyl with a base such as an alkali metal (e.g. sodium hydroxide) in a solvent such as methanol to yield the desired compound of formula XXI.

A compound of formula IV can be made by (1) treating a corresponding compound of formula XXII with a reducing agent such as tin(II) chloride, in the presence of an aqueous acid such as acetic acid, thereby reducing the nitro group to obtain the corresponding amine, followed by (2) treating the amine thereby formed with a combination of nitrous acid and sulfuric acid to effect diazotization at the amine group, and thereafter (3) treating the diazotized compound with a copper(I) halide such as cuprous bromide, CuBr.

A compound of formula V, wherein A-B is ethynylene, can be made by treating a corresponding compound of formula XXIa, wherein Y is carbonyl and Pr is trimethylsilyl, with a fluoride base (for example, TBAF) and an acid chloride of formula $R^1$—CO—Cl, thereby making the desired compound. A compound of formula V, wherein A-B is vinylene, can be made by reducing the product thus obtained, as previously described.

A compound of formula VI can be made by treating a corresponding compound of formula XXIa wherein Pr is trimethylsilyl with a base (for example, TBAF) and an alkyl carbonate of formula $(R^3)_2CO$ wherein $R^3$ is a lower alkyl group, or an alkyl chloroformate of formula ClCOOR$^3$, thereby making the desired compound A compound of formula VI can, alternatively, be made by treating a corresponding compound of formula XXIa wherein Pr is trimethylsilyl with TBAF and carbon dioxide and esterified with a lower alcohol of formula R$^3$OH.

A compound of formula VII can be made by treating a corresponding compound of formula XXIV with iron dust and concentrated hydrochloric acid in 95% ethanol to reduce the nitro group and thereby form the corresponding amine. The amine can then be treated with a nitrite (such as t-butyl nitrite) to form the corresponding diazonium salt which can in turn be treated with a copper(I) salt (such as copper(I) bromide or copper(I) chloride) to displace the diazonium group and form the corresponding bromide or chloride. The diazotization and displacement reactions can be conducted in a solvent such as acetonitrile and at a temperature of from 0° to 25° C.

A compound of formula VIII can be made by reacting a corresponding ketone having the formula R$^1$—CO—R$^2$ with an alkali metal acetylide (for example lithium acetylide) or alkaline earth metal acetylide (for example magnesium acetylide). The reaction can be conducted in a solvent such as THF, diethyl ether, or DME and at a temperature of about $-100°$ to about 25° C.

A compound of formula IX can be made by reacting a corresponding compound of formula VII with trimethylsilylacetylene in the presence of a catalyst such as a combination of bis(triphenylphosphine)palladium dichloride and copper(I) iodide in diethylamine or triethylamine, followed by treatment with a base (for example, an alkali metal hydroxide such as sodium or lithium hydroxide) in a lower alcohol as solvent to effect removal of the trimethylsilyl group.

Compounds having formula XII and XIII can be made along the lines set forth in Morris et al., J. Med. Chem., 34, 447–455, (1991).

A compound of formula XIV can be made by reacting a sulfide of formula X-SH with a corresponding compound having formula IV in the presence of a catalyst such as copper bronze and a base such as an alkali metal hydride (e.g. sodium hydride). The reaction can be conducted in a solvent such as THF at reflux.

A compound of formula XV can be made by reacting a corresponding aniline of formula XXV with an acid of formula XXVI in the presence of a coupling reagent. Suitable coupling reagents generally known in the art as standard peptide coupling reagents can be employed, for example thionyl chloride (see Morris et al., supra) or carbonyldiimidazole (CDI). The reaction can be conducted in a solvent such as dimethylacetamide, dichloromethane, benzene, THF, and DMF, and at a temperature in the range of about $-40°$ to 40° C.

A compound of formula XVI can be made by treating a corresponding ketone having the formula R$^1$—CO—R$^2$ with the ylide derived from the reaction of a trimethylsulfonium salt (such as trimethylsulfonium iodide) with a base (such as an alkali metal hydroxide). The reaction can be conducted in a one-pot process employing a solvent such as dichloromethane.

A compound of formula XVII can be made by diazotizing a corresponding aniline of formula XXV, as previously discussed, and heating in dilute sulfuric acid to form the corresponding phenol. The corresponding thiophenol can be formed by reacting an excess of methanethiol in the presence of sodium hydride with a corresponding compound of formula VII wherein G is a leaving group such as chloro.

A compound of formula XVIII can be made by treating a corresponding compound of formula XXVII wherein R$^6$ is a halo group with a corresponding compound of formula XXVIII, wherein R$^4$ is hydroxy, thiohydroxy, or amino, optionally in the presence of a catalyst such as copper bronze and a base such as an alkali metal hydride. The reaction can be conducted at reflux in a solvent such as THF.

A compound of formula XIX can be made by (1) treating a compound of formula XXIX with a protective reagent such as trimethylsilyl chloride in a solvent such as dichloromethane and at a temperature of from about $-78°$ to about 25° C.; (2) treating the protected compound thus obtained with a suitable reducing agent such as lithium aluminum hydride in a solvent such as diethyl ether or THF and at a temperature of about 0° to about 25° C., thereby reducing the carbonyl group to methylene; followed by (3) treating the reduced product with trifluoromethylsulfonic anhydride in the presence of a base such as triethylamine, in a solvent such as dichloromethane, and at a temperature of about $-78°$ C. to about 25° C., thereby yielding the desired compound.

An epoxide of formula XXXII may be prepared from a diol of formula XXXI using a suitable dehydrating agent, for example bis[α,α-bis(trifluoromethyl)benzenemethanolato]diphenylsulphur. Suitable conditions for the preparation of a epoxide of formula XXXII are given in Example 13.e.

A diol of formula XXXI may be prepared from a ketone of formula XXX by reduction. The reduction may be carried out using a suitable reducing agent, for example a hydride, such as sodium borohydride. Convenient conditions for the preparation of a diol of formula XXXI are given in Example 13.d.

A ketone of formula XXX may be prepared from a toluene of formula XXXIII by deprotonation and treatment with an amide of formula XXXIV, in which R$^7$ and R$^8$ are each independantly lower alkyl, or in which R$^7$ and R$^8$ when taken together with the atoms to which they are attached form a 5-7 membered ring. The deprotonation of the toluene may be carried out with a suitable base, for example lithium diisopropyl amide. The reaction may be carried out in a suitable organic solvent, for example, an ether such as tetrahydrofuran. The reaction may be carried out at a suitable temperature, for example a temperature in the range of $-78°$ C. to 100° C. Convenient conditions for the preparation of a ketone of formula XXX are given in Example 13.a.–13.c.

An amide of formula XXXIV may be prepared from an acid of formula XXVI or a reactive derivative thereof by reaction with the appropriate amine. The reaction may conveniently be carried out for example as described in Example 13.a.

A diol of formula XXXV may be prepared by (a) treating a ketone of formula XIII with a base such as LDA, lithium hexamethyldisilazide(LHMDS), or tetramethylpiperadide, in a solvent such as THF, diethyl ether, or DME, followed by addition of a ketone having the formula R$^1$—CO—R$^2$ (aldol condensation), and at a temperature of about $-100°$ to about 25° C., followed by (b) reduction of the carbonyl group to alcohol with a reducing agent such as sodium borohydride or lithium aluminum hydride at a temperature of from about 0° to about 25° C.

Examples of suitable pharmaceutically acceptable salts are organic acid addition salts formed with acids which form a physiologically acceptable anion, for example, tosylate, methanesulfonate, acetate, tartrate, citrate, succinate, benzoate, ascorbate, α-ketoglutarate, and α-glycerophosphate. Suitable inorganic salts may also be formed such as sulfate, nitrate, and hydrochloride. Pharmaceutically acceptable salts may be obtained using standard procedures well known in the art, for example by reacting a compound of formula I with a suitable acid affording a physiologically acceptable anion. It is also possible with some compounds of the invention to make a corresponding alkali metal (for example, sodium, potassium, or lithium) or alkaline earth metal (for example, calcium) salt.

In vivo hydrolyzable esters of compounds of the invention can be made by treating a parent tertiary carbinol of formula I with an appropriate acid chloride (for example, acetyl chloride, propionyl chloride, or benzoyl chloride) or acid anhydride (for example, acetic anhydride, propionic anhydride, trifluoroacetic anhydride, or benzoic anhydride) in the presence of a suitable base such as triethylamine. Catalysts such as 4-dimethylaminopyridine can also be usefully employed.

When an optically-active form of a compound of formula I is desired, it may be prepared by resolution of a racemic or less optically-pure form of a compound of formula I; for example, resolution may be carried out using steps similar those described in Example 12 (and sub-parts thereof). Alternatively, an optically active compound of formula I may be prepared by synthesis from optically-active starting materials, by chiral synthesis, or by chromatographic separation using a chiral stationary phase. The preparation from optically active starting materials may be carried out for example as described in Examples 13 and 14.

As described hereinabove, the compounds according to the invention are useful in the treatment of urinary incontinence, more specifically urge incontinence, which includes for example detrusor instability, which may result from cystitis, urethritis, tumours, stones, diverticuli or outflow obstruction; and detrusor hyperreflexia, which may result from stroke, dementia, Parkinsons, suprasacral spinalcord injury or spurasacral spinalcord disease.

When used to treat urinary incontinence, a compound of formula I is generally administered as an appropriate pharmaceutical composition which comprises a compound of formula I as defined hereinbefore together with a pharmaceutically acceptable diluent or carrier, the composition being adapted for the particular route of administration chosen. Such compositions are provided as a further feature of the invention. They may be obtained employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous, intravesicular (directly into the bladder), subcutaneous or intramuscular injection or infusion; or in the form of a patch for transdermal administration.

The dose of compound of formula I which is administered will necessarily be varied according to principles well known in the art taking account of the route of administration, the severity of the incontinence condition, and the size and age of the patient. In general, a compound of formula I will be administered to a warm blooded animal (such as man) so that an effective dose is received, generally a daily dose in the range of about 0.01 to about 10 mg/kg body weight. For example, if the compound is administered intravesicularly, it is administered in the range of about 0.01 to about 5 mg/kg body weight. If it is administered orally, it is administered in the range of about 0.01 to about 10 mg/kg body weight.

It will be apparent to those skilled in the art that a compound of formula I can be co-administered with other therapeutic or prophylactic agents and/or medicaments that are not medically incompatible therewith. Compounds within the scope of the invention do not show any indication of untoward side-effects in laboratory test animals at several multiples of the minimum effective dose.

The actions of compounds of formula I as smooth muscle relaxants useful as therapeutic agents for the treatment of urinary incontinence through their action to open potassium channels and hyperpolarize the membrane electrical potential in bladder detrusor smooth muscle can be shown using suitably designed in vitro tests, such as the one described following. In general, compounds according to the invention have been found to exhibit activity at 30 μM (micromolar) or less in the test. The compounds exemplified herein have all been found to exhibit an $IC_{50}$ on the order of 30 μM or less in the test. For example, the compounds of Examples 6 and 8 exhibited $IC_{50}$'s of 7.8 and 13.6, respectively. "$IC_{50}$" is a well understood term and means the concentration of test compound which causes a 50% decrease in the in vitro contraction of the bladder tissue described in the following test.

Male albino Hartley guinea pigs (450–500 g) are sacrificed by carbon dioxide induced asphyxiation and quickly exsanguinated. The lower abdominal cavity is opened and the urinary bladder isolated. The bladder is cleaned of surrounding connective and adipose tissue, and the portion above the ureteral orifices is removed and washed in Krebs-Henseleit buffer solution of the following composition (in mM): NaCl 118.0, KCl 4.7, $MgSO_4$ 1.2, $KH_2PO_4$ 1.2, $CaCl_2$ 2.5, $NaHCO_3$ 25.0 and d-glucose 11.1. The solution is warmed to 37° C. and gassed with 95% $O_2$ and 5% $CO_2$. With vigorous bubbling, the solution should have a pH value close to 7.4.

The dome of the washed bladder is cut off and discarded; the remaining bladder is placed on a gauze in a Petri dish containing the buffer solution. A mid-ventral longitudinal cut is made with scissors to open the bladder. The strips cut from the dome and the base edge are discarded. The remaining detrusor mid-section is cut into two horizontal strips with an approximate width of 2.0 mm. These two strips are further bisected at the mid-dorsal section, creating four strip of similar dimensions. Each strip thus contains both dorsal and ventral portions of the bladder.

The two ends of each individual strip are tied to a glass support rod and a force-displacement transducer (Grass model FT03), respectively, with 4-0 black braided silk suture.

The transducers are connected to a polygraph (Grass model 7E), which is calibrated at 5 mV/cm and the calibration checked for linearity with weights of 5 and 0.5 grams. The analog electrical output signals from the polygraph are digitized by a Modular Instrument Micro 5000 signal processing system using Biowindow Data Acquisition Software, which is run under the Microsoft OS/2 operating system with an IBM-compatible PC.

The detrusor strips on the glass rod are secured in 20 ml tissue baths and allowed to equilibrate under a preload tension of 2 grams. During the following 45 to 60 min equilibration period, the tissue is washed with fresh buffer solution at 15 min interval, with the tension adjusted, if necessary, to 2 grams prior to washing. After the equilibration period, a priming dose of 15 mM KCl (total concentration in the bath) is applied. The tissue is washed after 10 min and washed twice more at 15 min intervals with tension adjusted to 2 grams before each washing.

When the tissue relaxes to a steady state after the final washing, 15 mM KCl is again applied. Once the myogenic activity of the tissue reaches a steady state, the baseline data are acquired through the Biowindows Data Acquisition System by averaging 5 min of the myogenic data sampled at 32 Hz. Once the baseline is acquired, the experimental compounds are dosed in a cumulative manner in half log unit increments. The contact time for each dose is 10 min with the final 5 min being the period of time that the dose response data are acquired. If 30 $\mu$M of the test compound does not abolished the detrusor mechanical activity, then 30 $\mu$M cromakalim, a putative potassium channel opener, is dosed to establish a maximum response. The effect of the compound at each dose is expressed as % of the maximum inhibitory response, which is further normalized with respect to the corresponding effect of the compound vehicle control. The normalized response is then used to derive the $IC_{50}$ of the relaxant activity of the compound through the application of Marquardt's nonlinear iterative curve fitting technique to a standard dose-response function.

The ability of compounds according to the invention to open potassium channels in detrusor smooth muscle can be further demonstrated by a second in vitro test.

This second in vitro test is similar to the one described above with regard to tissue preparation and data acquisition. However, the following exceptions are noted. In this second test, the contraction of the detrusor strips during priming and after the equilibration period is achieved with 80 mM instead of 15 mM KCl (total concentration in the bath). A sustained tension in the tissue is evident after this high KCl stimulation, because voltage-sensitive calcium channels have been rendered open to permit an influx of calcium into the cells and the development of tonic tension. This tension is totally abolished with 300 $\mu$M of papaverine, which is thereby used to establish the maximum response in this test.

Typical calcium channel blockers like nifedipine, nimodipine, isradipine, and verapamil are able to relax and reduce the myogenic activity of guinea pig detrusor strips in both tests by virtue of their blocking action on calcium channels. However, all of the aforementioned calcium channel blockers are more potent in the second test when 80 mM KCl is used, than in the first test where 15 mM KCl is used. In contrast, while the putative potassium channel opener cromakalim has a potent relaxant activity in the first test with an $IC_{50}$ in the range of 0.6 to 0.9 $\mu$M, it demonstrates insignificant relaxant activity in the second test at concentrations as high as 30 $\mu$M. Thus, the profile of a higher relaxant activity in the first test than in the second of compounds according to the invention indicates that the compounds are functioning as potassium channel openers.

The ability of the compounds according to the invention to act as potassium channel openers on bladder tissue may be further demonstrated by a standard test which measures the effect of test compounds on the rate of efflux of rubidium from the tissue.

It will be further appreciated by those skilled in the art that the efficacy of compounds according to the invention can be demonstrated by standard assays in vivo. The following is a description of such a standard test.

Male Wistar rats weighing 450-550 grams are anesthetized with 20 mg/kg, i.p. Nembutal and 80 mg/kg, i.p. Ketamine. The trachea is cannulated to prevent airway obstruction. Body temperature is maintained by means of a heating pad. The right jugular vein is cannulated for drug administration. The urinary bladder is exposed through a midline abdominal incision and emptied of urine by application of slight manual pressure. A catheter (PE 50) is inserted through the apex of the bladder dome around 3-4 mm into its lumen and tied with suture (4-0 silk) to prevent leakage. The bladder catheter is connected to a pressure transducer for the measurement of bladder pressure. The bladder is then placed back into the abdominal cavity and the incision is stitched closed except where the catheter exits the cavity. The bladder is allowed to equilibrate for approximately 15 minutes. After the equilibration period, the rats are infused with saline directly into the bladder at a rate of 0.05 ml/min for the entire time of the experiment. The bladder pressure is then monitored for the start of bladder contractions. When the contractions start, the animal is then allowed to stabilize its pattern of contractions around 30 to 45 minutes before drug administration.

The test compounds are given i.v. The efficacy of a test compound is measured by comparison to the known reference drug cromakalim (SmithKline-Beecham) which is administered i.v. over the dose range of 0.05 to 0.5 mg/kg.

The above in vivo assay enables an assessment of the cystometric activity of test compounds. Micturition contractions are induced by a slow continuous infusion of saline directly into the bladder. The average change (in seconds from control) in the duration of the intercontraction interval (the time between contractions) over an approximate 20-min period is reported for each compound.

The following is a description of a test in vivo which is complimentary to the above described tests and which can be used to ascertain if a test compound is active and, additionally, if the test compound exhibits selectivity for the bladder without significant cardiovascular effects when dosed orally. For example, the compounds of Examples 5 and 12 were active and selective in this test when dosed at 3 mg/kg.

Male Wistar rats (400-500 g) were anesthetized with 50 mg/kg Nembutal, i.p. For each rat, the abdominal region and the front and back of the neck were shaved and povidone-iodine was applied to the skin. For carotid catheterization, the left carotid artery was exposed via a small ventral cervical incision. The exposed area was flushed with a 2% lidocaine HCl solution to relax the vessel. The catheter, filled with 0.9% saline, was introduced approximately 2.4 cm into the artery so that its tip resided in the aortic arch. The distal end of the catheter was exteriorized at the nape of the neck, filled with heparin (1000 units/ml) and heat sealed. For bladder catheterization, the catheters were implanted according to the method of Yaksh TL, Durant PAC, Brent CR. Micturition in rats: A chronic model for study of bladder function and effect of anesthesia. Am. J. Physiol. 251 (Regulatory Integrative Comp. Physiol. 20): R1177-R1185, 1986. The bladder was exposed through a midline abdominal incision. A trocar was passed through the abdominal muscle about 1 cm from the upper end of the incision and then tunneled subcutaneously to emerge through the skin at the back of the neck. A saline-filled catheter was passed through the trocar. A small opening in the bladder dome was created with an Accu-Temp cautery. The catheter was placed into the bladder and secured with a 4-0 silk ligature. The catheter was flushed with saline and patency was noted. The external end of the catheter was heat-sealed to prevent urine leakage. The abdominal muscles and the skin were sutured. Both catheters were threaded through a stainless steel anchor button (Instech), which was then sutured to the subcutaneous muscle at the point of exteriorization. The skin was sutured closed over the button. The animals were allowed to recover from anesthesia.

24-48 hours after surgery, each rat was placed in a metabolism cage and connected via the anchor button to an Instech spring tether and swivel system to protect the catheters from damage and to allow the animal free movement in the cage. The carotid catheter was connected to a Gould P23XL pressure transducer for blood pressure measurement. The bladder catheter was connected to a pump for saline infusion and to a pressure transducer by means of PE50 tubing and a 4-way stopcock. A toploading balance with a collection cup was placed under the cage for urine output measurement.

The rats were weighed, orally sham-dosed (dosing needle introduced, but no fluid expelled), and transvesical saline infusion (.18 ml/min) was begun and continued throughout the experiment. Variations in blood pressure, heart rate, intravesical pressure and urine output were recorded on either a Grass Polygraph or a Gould TA4000 recording system. The animals were allowed to equilibrate until the micturition pattern became consistent (approx. 45-90 min.). At this point, a basal level of each experimental parameter was recorded and the rats were administered by oral garage the appropriate dose of compound (in a 75% PEG 400-saline vehicle) in concentrations such that the volume was 1 ml/kg body weight. The effects of the compounds on experimental parameters were followed for five hours after administration. Cromakalim (Smithkline-Beecham) was used as the reference standard.

Experimental results for both the interval between contractions and also heart rates were expressed as the mean ± S.E.M. % change from basal level, with each animal serving as its own control. MAP is expressed as mean ± S.E.M mm Hg change from basal level.

Compounds according to the invention are active in one or more of the above-described tests.

The invention will now be illustrated by the following non-limiting examples in which, unless stated otherwise:
  (i) temperatures are given in degrees Celsius (° C.); operations were carried out at room or ambient temperature, that is, at a temperature in the range of 18°-25° C.;
  (ii) organic solutions were dried over anhydrous magnesium sulfate; evaporation of solvent was carried out using a rotary evaporator under reduced pressure (600-4000 pascals; 4.5-30 mm Hg) with a bath temperature of up to 60° C.;
  (iii) chromatography means flash chromatography on silica gel; thin layer chromatography (TLC) was carried out on silica gel plates;
  (iv) in general, the course of reactions was followed by TLC and reaction times are given for illustration only;
  (v) melting points are uncorrected and (dec) indicates decomposition; the melting points given are those obtained for the materials prepared as described; polymorphism may result in isolation of materials with different melting points in some preparations;
  (vi) final products had satisfactory proton nuclear magnetic resonance (NMR) spectra;
  (vii) yields are given for illustration only and are not necessarily those which may be obtained by diligent process development; preparations were repeated if more material was required;
  (viii) when given, NMR data is in the form of delta values for major diagnostic protons, given in parts per million (ppm) relative to tetramethylsilane (TMS) as an internal standard, determined at 300 MHz using perdeuterio dimethyl sulfoxide (DMSO-$d_6$) as solvent; conventional abbreviations for signal shape are used; coupling constants (J) are given in Hz; Ar designates an aromatic proton when such an assignment is made;
  (ix) chemical symbols have their usual meanings; SI units and symbols are used;
  (x) reduced pressures are given as absolute pressures in pascals (Pa); elevated pressures are given as gauge pressures in bars;
  (xi) solvent ratios are given in volume:volume (v/v) terms;
  (xii) mass spectra (MS) were run with an electron energy of 70 electron volts in the chemical ionization (CI) mode using a direct exposure probe; where indicated ionization was effected by electron impact (EI) or fast atom bombardment (FAB); values for m/z are given; generally, only ions which indicate the parent mass are reported; and
  (xii) optical rotations were measured at the sodium D line in a 1 dm cell; concentration "c" is reported in g/100 mL.

EXAMPLE 1

1,1,1-Trifluoro-2-methyl-3-(4-benzoylphenoxy)propan-2-ol.

A suspension of trimethylsulfoxonium iodide (8.57 g, 38.9 mmol) in 50 mL of dichloromethane cooled to 0° C. was treated with a solution of KOH (2.18 g, 38.9 mmol) in water (40 ml). The ylide was treated with trifluoroacetone (4.36 g, 38.9 mmol) and the reaction was maintained at 0° C. for 0.5 hours followed by reflux for 1.5 hours. The reaction was cooled to 0° C. and treated with a solution of 4-Hydroxybenzophenone (7.72 g, 38.9 mmol), KOH (2.18 g, 38.9 mmol) in water/ethanol (40 ml/5 ml). The mixture was treated with N-benzyltrimethylammonium hydroxide (8.46 g, 50.6 mmol) and then refluxed for 18 hours. The mixture was poured into ice-water and extracted with dichloromethane. The combined extracts were dried and evaporated to yield a brown oil. Chromatography of this oil, eluting with dichloromethane/hexane/ethyl acetate provided the title compound as a white solid (1.7 g); mp 70°-73°

C. NMR: 1.45 (s,3, CH$_3$), 4.16 (q,2, CH$_2$), 6.44 (s,1, OH), 7.16 (dd,2, J=7,2, Ar), 7.65 (m,7, Ar); MS: m/z=325(M+1). Analysis for C$_{17}$H$_{15}$F$_3$O$_3$: Calculated: C, 62.96; H, 4.66; Found: C, 62.71: H, 4.61.

EXAMPLE 2

1,1,1-Trifluoro-2-methyl-3-(4-phenylsulfonylphenoxy)-propan-2-ol

A suspension of trimethylsulfoxonium iodide (1.6 6 g, 7.56 mmol) and sodium hydride (0.36 g, 7.56 mmol of 50% in oil) was stirred in 25 mL of dimethylsulfoxide for 25 minutes. The mixture was cooled to 10° C. and was treated with a solution of trifluoroacetone (0.72 g, 6.41 mmol) in tetrahydrofuran (3 mL). After stirring for 20 minutes, the solution was allowed to warm to room temperature where it was treated with a solution of 4-(phenylsulfonyl)phenol (1.5 g, 6.40 mmol) and sodium hydride (0.31 g, 6.4 .mmol of 50% in oil) in dimethylsulfoxide (7.5 mL). The mixture was stirred for 1 hour and then heated to 50° C. for 18 hours. The reaction was poured into water, acidified to pH 6, and extracted with diethylether. The combined organic fractions were evaporated to give an oil. Chromatography, eluting with dichloromethane yielded the title compound as a tan solid (0.22 g); mp 94°–96° C.; NMR: 1.39 (s,3, CH$_3$), 4.12 (q,2, CH$_2$), 6.39 (s,1, OH), 7.17 (s,1, Ar), 7.20 (s,1, Ar), 7.63 (m,3, Ar), 7.91 (m,4, Ar); MS: m/z=361(M+1). Analysis for C$_{16}$H$_{15}$F$_3$O$_4$S: Calculated: C, 53.33; H, 4.20; Found: C, 53.54: H, 4.25.

EXAMPLE 3

1,1,1-Trifluoro-2-methyl-3-(4-phenylsulfonylphenylthio)propan-2-ol.

Potassium hydroxide (0.129 g, 2.3 mmol) in water (2 mL) was added dropwise to a stirred suspension of trimethylsulfoxonium iodide (0.476 g, 2.2 mmol), trifluoroacetone (0.258 g, 2.3 mmol) in dichloromethane (5 mL) under nitrogen at 0° C. The mixture was stirred for 0.5 hours and was then refluxed for a further 0.5 hour. After cooling to room temperature a solution of 4-(phenylsulfonyl)thiophenol (0.5 g, 2 mmol), potassium hydroxide (0.112 g, 2 mmol), and water (5 mL) was added in one portion and the mixture was stirred for 2 hours. The reaction mixture was diluted with dichloromethane, washed (saturated aqueous ammonium chloride solution, water, brine), and dried (Na$_2$SO$_4$). Evaporation gave an oil that crystallized from ether/ethyl acetate/hexane to give a white solid. The filtrate was evaporated to give a solid which was recrystallized from ether/hexane to give the title compound (0.24 g); mp 100°–102° C.; NMR: 1.35 (s,3, CH$_3$), 3.35 (m,2, SCH$_2$), 6.41 (s,1, OH), 7.57 (d,2, J=9, Ar), 7.67 (m,3, Ar), 7.83 (d,2, J=8.7, Ar), 7.94 (d,2, J=6.9, Ar). MS: m/z=377 (M+1). Analysis for C$_{16}$H$_{15}$F$_3$O$_3$S$_2$: Calculated: C, 51.06; H, 4.02; Found: C, 51.50: H, 3.94.

The starting 4-(phenylsulfonyl)thiophenol was prepared as follows:

A mixture of 4-chlorophenylphenylsulfone (4.5 g, 17.8 mmol), sodium methylthiolate (3.8 g, 54 mmol) and dimethylpropyleneurea (DMPU, 22 mL) was stirred at 100° C. for 18 hours. Excess 6M hydrochloric acid was added to the cooled reaction mixture which was then extracted with ethyl acetate. The combined oraganic extracts were washed (water, brine), dried and evaporated to give an off-white solid. Crystallization from ether/hexane gave the thiophenol (3.5 g, 80%) as colorless needles; mp 117°–119° C.; NMR: 6.23 (broad s,1, SH), 7.5 (d,2, J=8.7, Ar), 7.62 (m,3, Ar), 7.78 (d,2, J=6.9, ArH), 7.94 (d,2, J=9.9, Ar); MS: m/z=251(M+1).

EXAMPLE 4

1,1,1-Trifluoro-2-methyl-3-(4-phenylsulfonylphenylamino)propan-2-ol.

To a solution of N-(4-phenylsulfonylphenyl)-3,3,3-trifluoro-2-hydroxy-2-methylpropanamide (0.5 g, 1.33 mmol) in tetrahydrofuran (10 mL) at 0° C. was added a solution of borane in tetrahydrofuran (3.14 mL of 1.0M, 3.14 mmol) in a dropwise manner. The mixture was stirred at 0° C. for 15 minutes and was then refluxed for 18 hours. Excess borane was quenched by the careful addition of methanol. Evaporation of the mixture gave a white solid. The solid was partitioned between an aqueous sodium bicarbonate solution and dichloromethane. The combined organic extracts were dried and evaporated to yield the title compound (0.16 g); mp 145°–146° C.; NMR 1.27 (s,3, CH$_3$), 3.32 (d,2, CH$_2$), 6.13 (s,1, OH), 6.70 (m,1, NH), 6.82 (d,2, J=8.8, Ar), 7.58 (m,5, Ar), 7.84 (d,2, J=7.7, Ar); MS: m/z=360 (M+1). Analysis for C$_{16}$H$_{16}$F$_3$NO$_3$S.0.75 H$_2$O: Calculated: C, 51.54; H, 4.73; N, 3.76; Found: C, 51.63; H, 4.38; N, 3.70.

The starting N-(4-phenylsulfonylphenyl)-3,3,3-trifluoro-2-hydroxy-2-methylpropanamide was prepared as follows:

To a stirred, cooled (−20° C.) solution of 3,3,3-trifluoro-2-hydroxy-2-methylpropanoic acid (3.96 g, 25 mmol) in N,N-dimethylacetamide (36 mL) was rapidly added thionyl chloride (3.10 g, 26 mmol) and the mixture (a precipitate formed after a few minutes) stirred at −15° C. to −5° C. for one hour. 4-phenylsulfonylaniline (3.97 g, 17 mmol) was then added in one portion and the mixture allowed to stir at room temperature overnight. The solution was poured into water and the resulting solid was filtered off, washed (3M HCl, water), and dried at 65° C. for 2 hours. The solid was dissolved in 300 mL of refluxing dichloromethane as it boiled off. When 250 mL of hexane had been added (precipitate formed at about 180 mL addition) the mixture was concentrated to 250 mL and refrigerated. The yield of light tan solid was 5.92 g (93%); mp 164°–166° C.; 250 MHz NMR: 1.59 (s,3, CH$_3$), 7.57–7.72 (m,4, OH, Ar), 7.92–8.04 (m,6, Ar), 10.43 (s,1, NH). Analysis for C$_{16}$H$_{14}$F$_3$NO$_4$S: Calculated: C, 51.47; H, 3.78; N, 3.75; Found: C, 51.22; H, 3.83; N, 3.72.

EXAMPLE 5

4,4,4-Trifluoro-3-hydroxy-3-methyl-1-(4-phenylsulfonylphenyl)-trans-but-1-ene.

To a stirred solution of 1-(4-phenylsulfonylphenyl)-3-hydroxy-3-methyl-4,4,4-trifluorobut-1-yne (0.45 g, 1.27 mmol) in tetrahydrofuran (6 mL) was added lithium aluminum hydride (56 mg, 1.4 mmol) in one portion and the reaction mixture stirred for 18 hours. The reaction mixture was then treated sequentially with water (0.4 mL), 2N sodium hydroxide (0.4 mL), and water (1 mL). After 10 minutes of stirring the reaction was filtered through diatomaceous earth and the precipitate washed with ethyl acetate. The aqueous layer of the filtrate was separated and extracted further with ethyl acetate. The combined organic extracts were dried filtered, and evaporated. The crude oil was purified by chromatography, with chloroform:ethyl acetate as eluent (18:1), to yield the title compound as a white solid (0.17 g, 37%);

mp 94°–97° C.; 250 MHz NMR (CDCl$_3$): 1.56 (s,3, CH$_3$), 2.30 (s,1, OH), 6.38 (d,1, J=16.0, vinylic), 6.89 (d,1, J=16.0, vinylic), 7.46–7.60 (m,5, Ar), 7.89–7.96 (m,4, Ar); MS (EI): m/z=356 (M+). Analysis for C$_{17}$H$_{15}$F$_3$O$_3$S: Calculated: C, 57.29; H, 4.24; Found: C, 57.24; H, 4.32.

Alternatively, the title compound can be prepared as follows.

To a solution of sodium bis(2-methoxyethoxy)aluminum hydride (1.5 mL, 3.4M in toluene) in freshly distilled diethyl ether (6 mL) was added a solution of 1-(4-phenylsulfonylphenyl)-3-hydroxy-3-methyl-4,4,4-trifluorobut-1-yne in diethyl ether (6 mL) dropwise. The rate of addition was controlled so that the reaction temperature did not exceed 8° C. The mixture was stirred for 15 minutes and was quenched at 0° C. with 3N sulfuric acid (15 mL). Water (10 mL) was added and the product was extracted into diethyl ether. The combined organic extracts were washed (brine) and dried. The solvent was evaporated and the material was purified by chromatography, with chloroform:diethyl ether (25:1) as the eluent, to give the title compound (848 mg, 79%).

EXAMPLE 6

4,4,4-Trifluoro-3-hydroxy-3-methyl-1-(4-phenylsulfonylphenyl)but-1-yne.

To a cooled (−78° C.) solution of 4-phenylsulfonylphenylethyne (66 mg, 0.27 mmol) in freshly distilled tetrahydrofuran (2.5 mL) was added n-BuLi (109 mL, 2.5M solution in hexanes, 0.27 mmol). The solution was stirred for 10 minutes at −78° C. at which time 1,1,1-trifluoroacetone (272 mL, 1.0M solution in tetrahydrofuran, 0.27 mmol) was added. The reaction mixture was kept at −78° C. for five minutes before quenching with 2N HCl. Diethyl ether was added, and the aqueous layer extracted further with diethyl ether. The combined organic layers were dried, evaporated and the product purified by chromatography, with ethyl acetate:hexanes as eluent (1:4) to yield the title butyne as a white solid (72 mg, 75%); mp 94.8°–95.3° C.; 250 MHz NMR (CDCl$_3$): 1.72 (s,3, CH$_3$), 3.08 (s,1, OH), 7.48–7.60 (m,5, Ar), 7.87–7.94 (m,4, Ar); MS: m/z=355(M+1). Analysis for C$_{17}$H$_{13}$F$_3$O$_3$S: Calculated: C, 57.62; H, 3.70; Found: C, 57.46; H, 3.65.

The starting 4-phenylsulfonylphenylethyne was prepared as follows:

To a solution of 4-phenylsulfonylbromobenzene (0.380 g, 1.28 mmol) in diethylamine (10 mL) was added trimethylsilylacetylene (212 mL, 1.5 mmol), bis[triphenylphosphine]palladium dichloride (70 mg, 0.1 mmol), and copper(I) iodide (5 mg, 0.05 mmol), respectively. After 1 hour, the solvent was evaporated. To the resulting black residue was added H$_2$O (5 mL) and this was extracted with ethyl acetate. The combined organic extracts were dried filtered and evaporated. The crude material was passed through a small plug of silica gel (1:1 ethyl acetate:hexanes as eluent), and the resulting solution was evaporated. The resulting material was dissolved in methanol (5 mL) and 1.0N potassium hydroxide (2 mL) was added. The mixture was stirred for 15 minutes and neutralized with 7.00 buffer. The product was partitioned from the aqueous solution by extraction with ethyl acetate and chloroform. The combined organic extracts were dried, evaporated and purified by chromatography, with ethyl acetate:hexanes as eluent (1:5) to yield the alkyne as a white solid (270 mg, 87%); NMR (CDCl$_3$): 3.24 (s,1), 7.49–7.60 (m,5, Ar), 7.88–7.96 (m,4, Ar); MS: m/z=243(M+1).

EXAMPLE 7

1-(4-Benzoylphenyl)-4,4,4-trifluoro-3-hydroxy-3-methylbut-1-yne.

To a cooled (−78° C.) solution of diisopropylamine (99 mL, 0.87 mmol) in freshly distilled tetrahydrofuran (5 mL) was added a solution of n-butyllithium (326 mL of a 2.5M solution in hexanes, 0.81 mmol). The solution was stirred at −78° C. for 25 minutes before a tetrahydrofuran solution of 4-benzoylphenylethyne (120 mg, 0.58 mmol) was added. The reaction was kept at −78° C. for an additional 20 minutes before 1,1,1-trifluoroacetone (521 mL, 5.8 mmol) was added in one portion. After stirring at −78° C. for 15 minutes the reaction was quenched by pouring into a saturated NH$_4$Cl solution. The product was extracted into diethyl ether. The combined ethers were dried and evaporated. The crude product was adsorbed onto silica gel and purified by chromatography, with ethyl acetate:hexanes as the eluent (gradient 1:9 to 1:3), to yield the title compound as a white solid after trituration with hexanes (80 mg, 43%); mp 94.5°–96.0° C.; 250 MHz NMR (CDCl$_3$): 1.76 (s,3, CH$_3$), 2.88 (s,1, OH), 7.46–7.64 (m,5, Ar), 7.77–7.79 (m,4, Ar); MS: m/z=319(M+1). Analysis for C$_{18}$H$_{13}$F$_3$O$_2$: Calculated: C, 67.92; H, 4.14; Found: C, 68.16; H, 4.15.

Alternatively, the title compound was prepared from the 1,3-propanediol-ketal of 4-benzoylphenylethyne using conditions similar to those described above. The ketal was formed by treatment of 4-benzoylphenylethyne with 1,3-propanediol and toslic acid in toluene under standard conditions. Following the coupling between the alkyne and the 1,1,1-trifluoroacetone, the ketal was removed using aqueous oxalic acid in dichloromethane.

The starting 4-benzoylphenylethyne was prepared as follows:

To a solution of 4-bromobenzophenone (1.31 g, 5.0 mmol) in diethylamine (50 mL) was added trimethylsilylacetylene (814 mL, 5.8 mmol), bis[triphenylphosphine]palladium dichloride (351 mg, 0.5 mmol), and copper(I) iodide (47.5 mg, 0.25 mmol), respectively. After 2 hours, the reaction was quenched with saturated NaHCO$_3$ and extracted with diethyl ether. The combined organic extracts were dried, filtered (diatomaceous earth and silica gel) and evaporated. The crude material was purified by chromatography, with diethyl ether:hexanes as the eluent (1:9). The resulting trimethylsilylacetylene was dissolved in methanol (50 mL) and 2.0N potassium hydroxide (8 mL) was added. The mixture was stirred for 1 hour before neutralization with 7.00 buffer. The methanol was evaporated and the product was partitioned from the aqueous solution by extraction with diethyl ether. The combined organic extracts were dried, evaporated, adsorbed onto silica gel and purified by chromatography with ethyl acetate:hexanes as the eluent (1:9), to yield the alkyne as a cream colored solid (588 mg, 57%); NMR (CDCl$_3$): 3.25 (s,1), 7.47–7.63 (m,5, Ar), 7.75–7.8 (m,4, Ar; MS: m/z=207(M+1).

EXAMPLE 8

4,4,4-Trifluoro-3-hydroxy-3-methyl-1-[4-(pyrid-4-ylsulfonyl)phenyl]-trans-but-1-ene.

To a solution of 4,4,4-trifluoro-3-hydroxy-3-methyl-1-[4-(pyrid-4-ylsulfonyl)phenyl]but-1-yne (0.32 g, 0.90 mmol) in dry tetrahydrofuran (5 mL) was added lithium aluminum hydride (44.4 mg, 1.17 mmol) portionwise over 1 minute and the suspension was stirred for 1 hour. The crude reaction mixture was treated sequentially with water (0.4 mL), 2N sodium hydroxide (0.4 mL), and water (1 mL). This mixture was stirred for 10 minutes, filtered through diatomaceous earth with ethyl acetate. The combined washings and filtrate were separated and the aqueous phase was extracted with ethyl acetate. The organic extracts were dried and evaporated. The crude oil was purified by chromatography with ethyl acetate:dichloromethane as the eluent (1:5) to yield the title compound as a white solid (60 mg, 18%); mp 168°–171° C.; NMR (CDCl$_3$): 1.59 (s,3, CH$_3$), 2.43 (s,1, OH), 6.41 (d,1, J=15.9, vinylic), 6.93 (d,1, J=15.9, vinylic), 7.56 (d,2, J=5.9, Ar), 7.76 (d,2, J=5.9, Ar), 7.93 (d,2, J=8.3, Ar), 8.82 (d,2, J=5.9, Ar); MS (EI): m/z=357(M+). Analysis for C$_{16}$H$_{14}$F$_3$NO$_3$S: Calculated: C, 53.77; H, 3.95; N, 3.92; Found: C, 53.41; H, 4.05; N, 3.84.

EXAMPLE 9

4,4,4-Trifluoro-3-hydroxy-3-methyl-1-[4-(pyrid-4-ylsulfonyl)phenyl]but-1-yne.

To a solution of diisopropylamine (0.37 mL, 2.66 mmol) in tetrahydrofuran (11 mL) at −20° C. was added n-butyllithium (0.9 mL of 2.5M solution in hexanes, 2.25 mmol) and the resulting solution was stirred for 25 minutes at −20° C. before being cooled to −78° C. To this was added a solution of 4-(4-pyridylsulfonyl)phenylacetylene (0.5 g, 2.05 mmol) in tetrahydrofuran (3 mL) over a five minute period. The mixture was stirred for an additional 15 minutes at −78° C. To this was added 1,1,1-trifluoroacetone (0.20 mL, 2.25 mmol) in one portion. After stirring the mixture at −78° C. for 20 minutes, it was quenched with water, warmed to ambient temperature and the pH adjusted to 7.0 with saturated aqueous NH4Cl . The solution was evaporated and the resulting residue was partitioned between water and ethyl acetate. The ethyl acetate layer was separated, washed (brine), dried and evaporated. The resulting brown oil was purified by chromatography, with ethyl acetate:dichloromethane as the eluent (1:5), to give the title compound as a white solid (0.36 g, 50%); mp 122°–125° C.; NMR (CDCl$_3$): 1.73 (s,3, CH$_3$), 3.37 (s,1, OH), 7.61 (d,2, J=8.2, At), 7.76 (d,2, J=5.1, Ar), 7.93 (d,2, J=4); MS: m/z=356(M+1). Analysis for C$_{16}$H$_{12}$F$_3$NO$_3$S: Calculated: C, 54.08; H, 3.40; N, 3.94; Found: C, 53.99; H, 3.41; N, 3.75.

The starting 4-(4-Pyridylsulfonyl)phenylacetylene was prepared as follows.

a. 4-(4-Pyridylthio)bromobenzene. To a solution of potassium hydroxide (0.34 g, 5.29 mmol) in methanol (35 mL) was added 4-bromobenzenethiol (1.0 g, 5.29 mmol) and the solution was stirred for 10 minutes. Evaporation of the methanol gave a solid which was dissolved in dimethylformamide (20 mL) and treated with 4-chloropyridine hydrochloride (0.4 g, 2.64 mmol). The resulting suspension was stirred at 80° C. for four hours. The reaction mixture was cooled to room temperature, poured into water and extracted with ethyl acetate. The combined ethyl acetate extracts were washed with 1N sodium hydroxide and water respectively, dried, and evaporated to give a light tan solid which was recrystalized from hexanes to yield the bromide as a light yellow crystalline solid (0.57 g, 82%); mp 68°–70° C.; NMR 9CDCl$_3$): 6.93–6.96 (m,2, Aromatic), 7.39–7.44 (m,2, Ar), 7.56–7.60 (m,2, Ar), 8.36–8.38 (m,2, Ar); MS (EI): m/z=267(M$^{30}$).

b. 4-(4-Pyridylsulfonyl)bromobenzene. A solution of potassium permanganate (0.71 g, 4.5 mmol) in water (10 mL) was added dropwise to a stirred solution of 4-(4-pyridylthio)bromobenzene (1.0 g, 3.75 mmol) in glacial acetic acid (15 mL) over a five minute period. The dark mixture was stirred an additional 20 minutes and treated with sodium thiosulfate (500 mg) to quench the excess potassium permanganate. The reaction mixture was filtered (diatomaceous earth) and the precipitate was washed with acetic acid (20 mL). The combined filtrate was evaporated to remove nearly all the acetic acid. The aqueous residue was diluted with water and extracted with ethyl acetate. The organic extracts were combined and washed (water, saturated sodium bicarbonate, water, brine), dried (Na$_2$SO$_4$) and evaporated to provide a crystalline solid. Purification by chromatography, with ethyl acetate:dichloromethane as the eluent (1:5) yielded the bromide (0.46 g, 39%); NMR (CDCl$_3$): 7.68–7.84 (m,6, Ar), 8.83–8.86 (m,2, Ar); MS (EI): m/z=299(M$^{30}$). Analysis for C$_{11}$H$_8$NO$_2$SBr: Calculated: C, 44.31; H, 2.70; N, 4.70; Found: C, 44.38; H, 2.72; N, 4.63.

c. 4-(4-Pyridylsulfonyl)phenylacetylene. To a suspension of cuprous iodide (16 mg, 0.08 mmol) and 4-(4-pyridylsulfonyl)bromobenzene (2.53 g, 8.48 mmol) in triethylamine (45 mL) and freshly distilled tetrahydrofuran (30 mL) was added bis(triphenylphosphine)palladium (II) chloride (0.12 g, 0.17 mmol) followed by trimethylsilylacetylene (1.44 mL, 10.2 mmol). The mixture was stirred for 18 hours and evaporated. The residue was dissolved in methanol (70 mL) and 1N potassium hydroxide (15 mL) was added; the reaction was stirred for two hours. The methanol was evaporated and the remaining aqueous suspension was extracted with ethyl acetate. The combined organic extracts were washed (brine), dried and evaporated to provide a brown solid product. The crude product was purified by chromatography, with ethyl acetate:hexanes as the eluent (gradient, 1:3 to 1:1), to give the acetylene (1.05 g, 51%).

EXAMPLE 10

4,4-Difluoro-3-difluoromethyl-3-hydroxy-1-(4-phenylsulfonylphenyl)but-1-yne.

Using a procedure similar to that described in Example 6, except substituting 1,1,4,4-tetrafluoroacetone for 1,1,1-trifluoroacetone, the title compound was prepared. Purification by chromatography, with ethyl acetate:hexane as the eluent (gradient, 25:75 to 30:70) gave the title compound as a white solid; mp 141.5°–142.1° C.; NMR (CDCl$_3$): 7.97–7.91 (m,4, Ar), 7.84–7.49 (m,5, Ar), 5.93 (t,2 J=55.8, CF$_2$H), 3.24 (s,1 OH); MS: m/z=373(M+1). Analysis for C$_{17}$H$_{12}$F$_4$O$_3$S: Calculated: C, 54.84; H, 3.25; Found: C, 54.87; H, 3.21.

EXAMPLE 11

4,4-Difluoro-3-difluoromethyl-3-hydroxy-1-(4-phenylsulfonylphenyl)-trans-but-1-ene.

To a stirred solution of 4,4-difluoro-3-difluoromethyl-3-hydroxy-1-(4-phenylsulfonylphenyl)but-1-yne (555 mg, 1.49 mmol) in tetrahydrofuran (15 mL) was added LAH (65 mg, 1.71 mmol) in one portion and the mixture was allowed to stir for 18 hours. The reaction was quenched with $Na_2SO_4.10H_2O$, filtered and evaporated. The resulting material was purified by chromatography, with diethyl ether:hexanes (60:40) as the eluent, followed by chromatography, with diethyl ether:hexanes (50:50) as the eluent. The resulting material was recrystalized from methyl tert-butylether:hexanes to give the title compound; mp 123.0°–123.5° C.; NMR ($CDCl_3$): 7.93–7.88 (m,4, Ar), 7.59–7.47 (m,5, Ar), 7.03 (d,1, J=16.2, vinylic), 6.33 (d,1, J=16.2, vinylic), 5.89 (t,2, J=54.8, $CF_2H$), 3.02 (s,1, OH); MS: m/z=375(M+1). Analysis for $C_{17}H_{14}F_4O_3S$: Calculated: C, 54.54; H, 3.77; Found: C, 54.30; H, 3.84.

EXAMPLE 12

(S)-(−)-4,4,4-Trifluoro-3-hydroxy-3-methyl-1-(4-phenylsulfonylphenyl)-trans-but-1-ene.

To a solution of (3S)-4,4,4-trifluor-3-methyl-3-[(S)-α-methylbenzylamino-carbonyloxy]-1-(4-phenylsulfonylphenyl)-trans-but-1-ene (4.9 g, 9.73 mmoles) and triethylamine (20.3 mL, 146 mmoles) in dichloromethane (60 mL) at 23° C. was added a solution of trichlorosilane (13.2 g, 97.3 mmoles) in dichloromethane (40 mL) dropwise over thirty minutes, and the mixture was allowed to reflux for seven hours. After cooling to ambient temperature, residual trichlorosilane was swept away using a nitrogen stream. The reaction mixture was treated with saturated aqueous ammonium chloride and stirred at 23° C. for two hours. The thick suspension was filtered and the filter cake washed with dichloromethane. The filtrate was transferred to a separatory funnel and the aqueous layer was washed with dichloromethane. The combined dichloromethane extracts were washed (water, brine), dried and evaporated. Chromatography, with chloroform:ethyl acetate as the eluent (20;1), gave a colorless oil which crystallized from hexane to yield the title compound as a white solid (2.83 g); $[\alpha]^{23}=-27.4$ (c=1.095, MeOH); mp 100°–102° C.; NMR: 1.56 (s,3, $CH_3$), 2.52 (s,1, OH), 6.38 (d,1, J=16.06, vinylic), 6.89 (d,1, J=16.06, vinylic), 7.46–7.60 (m,5, Ar), 7.89–7.96 (m,4, Ar); MS: m/z=357(M+1). Analysis for $C_{17}H_{15}F_3O_3S$: Calculated: C, 57.29; H, 4.24; Found: C, 57.29; H, 4.23.

A sample of the title compound, which had been obtained from a seperate preparation, was analyzed using a chiral high performance liquid chromatography column. From the chromatographic data and the measured rotation of the original sample, the rotation for the pure (S)-enantiomer of the title compound was estimated to be $[\alpha]=-28$.

The starting (3S)-4,4,4-trifluoro-3-methyl-3-[(S)-α-methylbenzylamino-carbonyloxy]-1-(4-phenylsulfonylphenyl)-trans-but-1-ene was prepared as follows.

A suspension of racemic 1-(4-phenylsulfonylphenyl)-3-hydroxy-3-methyl-4,4,4-trifluoro-trans-but-1-ene (11.6 g, 32.5mmol) and 4-dimethylaminopyridine (0.8 g, 6.5mmol) in toluene (110 mL) was treated with (S)-(−)-2-methylbenzylisocyanate (24.0 g, 163 mmol) in one portion. After heating the mixture at 100° C. (internal temperature) for 18 hours, additional (S)-(−)-2-methylbenzylisocyanate (10 g, 68 mmol) and 4-dimethylaminopyridine (0.8 g, 6.5 mmol) were added followed by heating at 90° C. for 48 hours. The crude reaction mixture was allowed to crystallize at 23° C. over two days. Filtration of the suspension and washing of the filter cake with toluene furnished highly enriched (S,S)-diastereomeric carbamate. Further purification of the carbamate was afforded by trituration with diethyl ether, followed by filtration of the suspension and washing of the filter cake with diethyl ether to yield 4.2 g of the desired diastereomeric carbamate. The combined diethyl ether washings and toluene filtrate from the original reaction mixture were concentrated, preabsorbed on silica, and purified by chromatography, with diethyl ether:hexane as the eluent (4:3), to provide an additional 2.1 g of the title compound. Total yield was 6.3 g of white solid, mp 174°–176° C., $[\alpha]^{23}=-48.2$ (c=0.518, $CH_3OH$); NMR: 1.49 (d,3, J=6.88, $CH_3$), 1.91 (s,3, $CH_3$), 4.75 (m,1, benzylic), 5.16 (m,1, NH), 6.29 (d,1, J=16.3, vinylic), 6.64 (d,1, J=16.3, vinylic), 7.30 (m,5, At), 7.49 (m,5, Ar), 7.89 (m,4, Ar); MS: m/z=503(M+1).

EXAMPLE 13

(S)-(−)-4,4,4-Trifluoro-3-hydroxy-3-methyl-1-(4-phenylsulfonylphenyl)-trans-but-1-ene.

2,3-Epoxy-1,1,1-trifluoro-2-methyl-4-(4-phenylsulfonylphenyl)butane (1.68 g) was dissolved in 250 mL ethanol and 150 mL 6N NaOH was added. The mixture was stirred for 2 hours, and 500 mL of saturated aqueous. $NaHCO_3$ was added. The mixture was extracted with ether and the organic layers were combined, dried, and evaporated to yield the title compound as a white solid (1.2 g, 70%); $[\alpha]^{23}=-28.35$ (c=1.05, MeOH); NMR ($CDCl_3$): 7.93–7.85 (m,4, Ar), 7.58–7.45 (m,5, Ar), 6.90–6.84 (d,1, vinylic), 6.40–6.34 (d,1, vinylic), 2.75 (s,1, OH), 1.55 (s,3, $CH_3$); MS: m/z=357(M+1).

The intermediate 2,3-epoxy-1,1,1-trifluoro-2-methyl-4-(4-phenylsulfonylphenyl)butane was prepared as follows.

a. (S)-(−)-3,3,3-Trifluoro-2-hydroxy-2-methylpropanoic acid. The solvent was removed in vacuo from a solution of racemic 3,3,3-trifluoro-2-hydroxy-2-methylpropanoic acid (316.2 g, 3.0 mole) and (S)-(−)-α-methylbenzylamine (363.5 g, 3.0 mole) in ethanol (1.5 L). The residue was triturated with toluene and the solid collected, washed (toluene) and dried under vacuum. Recrystallization from 10% n-butanol in toluene returned 126.0 g of 97% enantiomerically pure (97:3 by $^{19}F$ NMR) (S,S) salt, mp 161°–164° C. The solvent was removed from the recrystallization liquors and the residue was recrystallized three times from 10% n-butanol in toluene to yield an additional 24.0 g of 97% enantiomerically pure (by $^{19}F$ NMR) (S,S) salt, mp 162°–165° C. The 150.0 g of 97% enantiomerically pure salt was recrystallized twice from 10% n-butanol in toluene to yield 85 g of 99.5% enantiomerically pure (by $^{19}F$ NMR) (S,S) salt, mp 162.5°–164° C. 1H-NMR (300 MHz, $CDCl_3$): 1.25 (s,3, $CH_3$) 1.52 (d,3, J=6.8, $CH_3$) 4.16 (m,1, CH) 7.25–7.35 (m,5, At). [The (R,S) salt displays the acid $CH_3$ peak at 1.18 ppm and was not evident in this proton spectra]. $^{19}F$-NMR (376.5 MHz, $CDCl_3$): −79.83. [The (R,S) salt is shifted downfield by 13 Hz and was evident in this spectra at a level below the $^{13}C$ satellite peak (0.5%)]. The liquors from the recrystallization of the 97% enantiomerically pure salt were stripped in vacuo and the residue recrystallized three times from 10% n-butanol in toluene to yield an additional 31.5 g of 99% enantiomerically pure (by $^{19}$F NMR) (S,S) salt.

The 85 g of 99.5% pure (S,S) salt was partioned between aqueous HCl (105 mL of concentrated HCl and 700 mL of water) and ethyl ether (400 mL). The phases were separated and the aqueous phase was further extracted with ethyl ether (5×400 mL). The dried extracts (MgSO$_4$) were filtered and the solvent removed to yield 47.0 g of (S)-(−)-3,3,3-trifluoro-2-hydroxy-2-methylpropanoic acid, mp 105°–108° C., $[\alpha]_D^{23} = -18.9°$ (c=9.04, methanol); NMR (CDCl$_3$): 1.67 (s,3, CH$_3$); MS: m/z=159(M+1). Analysis for C$_4$H$_5$F$_3$O$_3$: Calculated: C, 30.39; H, 3.19; Found: C, 30.14; H, 3.19.

The 31.5 g of 99% pure (S,S) salt was likewise partioned between aqueous HCl and ethyl ether to yield 17.4 g of (S)-(−)-3,3,3-trifluoro-2-hydroxy-2-methylpropanoic acid, mp 107°–109° C.; $[\alpha]D_D^{23} = -18.7°$ (c=4.27, methanol).

b. (S)-α-Methyl-α-methoxy-3,3,3-trifluoro-2-hydroxy-2-methylpropanamide. A stirred solution of (S)-(−)-3,3,3-trifluoro-2-hydroxy-2-methylpropanoic acid (6 g, 38 mmol) and thionyl chloride (4.97 g, 42 mmol) in 350 mL dichloromethane was heated to reflux for 2 hours. The mixture was cooled to room temperature, and triethylamine (5.4 mL, 39 mmol) was added. The reaction mixture was heated to reflux for 45 minutes and cooled to room temperature. A solution of N-methyl-N-methoxyamine.HCl (5.55 g, 57 mmol), triethylamine (8 mL, 57 mmol) in 50 mL of dichloromethane was added. The mixture was allowed to stir overnight. The mixture was extracted with 3N HCl and the aqueous layers were combined and extracted with dichloromethane. The organic layers were dried and evaporated. The oil was distilled using a kugelrohr distillation apparatus (84° C., 26 Pa) to give a clear, colorless oil (6.6 g); NMR (CDCl$_3$): 5.31 (s,1), 3.74 (s,3), 3.35 (s,3), 1.66 (s,3); MS: m/z=202(M+1).

c. 3-Hydroxy-3-methyl-1-(4-phenylsulfonylphenyl)-4,4,4-trifluoro-2butanone. To a −78° C. solution of diisopropylamine (7.66 mL, 55 mmol), in 300 mL tetrahydrofuran was added BuLi (26 mL, 55 mmol) (diluted with 75 mL hexanes). 4-phenylsulfonyltoluene (11.55 g, 50 mmol) was dissolved in 100 mL tetrahydrofuran and slowly added to the reaction mixture. The temperature of the mixture was held below −40° C. The mixture was allowed to warm to 0° C., and was then cooled again to −78° C. (S)-(−)-N-methyl-N-methoxy-2-hydroxy-2-methyl-3,3,3-trifluoropropanamide (4 g, 20 mmol) was dissolved in 20 mL tetrahydrofuran and added to the reaction mixture in one portion. The mixture was allowed to stir for 1.5 hours and 400 mL aqueous saturated NH$_4$Cl was added. The mixture was extracted with dichloromethane and the organic layers were dried and evaporated. Chromatography, eluting with hexanes:ethyl acetate (75:25), then with hexanes:ethyl acetate (50:50), gave the desired ketone (5.18 g) as a white solid; $[\alpha]^{23}$ −36.23 (c=1.01,MeOH); mp 102.0°–103.5° C.; NMR (CDCl$_3$): 7.97–7.91 (m,4, Ar), 7.61–7.49 (m,3, Ar), 7.34–7.30 (d,2, Ar), 4.05 (s,1, OH), 1.64 (s,3, CH$_3$); MS: m/z=373(M+1).

d. (2S)-1,1,1-Trifluoro-2-methyl-4-(4-phenylsulfonylphenyl)-2,3-butanediol. To a stirred, cooled 0° C. solution of 3-hydroxy-3-methyl-1-(4-phenylsulfonylphenyl)-4,4,4-trifluoro-2-butanone (3.7 g, 10 mmol) in 135 mL methanol was added NaBH$_4$ (1.7 g, 44 mmol). The mixture was stirred for 15 minutes. 100 mL of saturated aqueous NH$_4$Cl was added. The mixture was extracted with dichloromethane and the combined organic layers were dried and evaporated. The resulting solid was pre-absorbed onto silica gel and purified by chromatography, with ether:hexane as the eluent (75:25), to give the title compound as a mixture of isomers (3.13 g, 83%); NMR (CDCl$_3$): 7.96–7.89 (m,4, Ar), 7.58–7.49 (m,3, Ar), 7.48–7.39 (d,2, Ar), 3.91–3.86 (m,2), 3.13 (s,1), 3.08 (s,1), 2.80 (s,1), 2.76–2.75 (d,1), 2.68 (s,1), 1.47 (s,3, CH$_3$); MS: m/z=375(M+1).

e. (2S)-2,3-Epoxy-1,1,1-trifluoro-2-methyl-4-(4-phenylsulfonylphenyl)butane. To a solution of bis[α,α-bis(trifluoromethyl)benzenemethanolato]diphenylsulfur (4.23 g, 6mmol) in 320 mL diethyl ether at 0° C. was added a solution of the diol product from Example 13.d. (1.81 g, 5 mmol) in 30 mL diethyl ether. The mixture was stired for 2 hours and evaporated. 200 mL of 20% aqueous KOH and 200 mL dichloromethane were added to the residue. The organic layer was separated and the aqueous layer was extracted with dichloromethane. The combined organic layers were dried and evaporated to give a residue, which was purified by chromatography, with dichloromethane:hexane (4:1) as the eluent, to give the epoxide as a mixture of isomers (1.68 g, 97%); NMR (CDCl$_3$): 7.97–7.91 (m,4, Ar), 7.60–7.49 (m,3, Ar) 7.42–7.38 (m,2, At); 5.30 (s,1), 3.43–3.40 (t,1), 3.12–3.06 (m,3), 2.17 (s,1), 1.49 (s,3, CH$_3$); MS: m/z=357(M+1).

EXAMPLE 14

(S)-(−)-4,4,4-Trifluoro-3-hydroxy-3-methyl-1-(4-phenylsulfonylphenyl)-trans-but-1-ene.

To a tetrahydrofuran (5 mL) solution of (2S)-1,1,1-trifluoro-2-methyl-4-(4-phenylsulfonylphenyl)-2,3-butanediol (product described in Example 13.d.) (500 mg, 1.34 mmol) was added sodium hydride (60 mg, 60% at dispersion, 1.57 mmol). The mixture was heated to 65° C. After 10 minutes, another aliquot of sodium hydride (60 mg, 60% oil dispersion, 1.57 mmol) was added. The mixture was heated to reflux (66° C. internal temp.) for 1.5 hours, after which time a third aliquot of sodium hydride (40 mg, 60% oil dispersion, 1.04 mmol) was added. The reaction was heated to reflux for 2.0 additional hours, then cooled to ambient temperature and stirred for an additional 1.6 hours. The reaction was quenched with water and the product extracted into diethyl ether. The organic extracts were dried and evaporated. The crude product was purified by chromatography, with diethyl ether:dichloromethane as the eluent (gradient, 0:100 to 2:98) to give the title compound as a white solid (326 mg, 68%). See Example 13 for characterization data.

EXAMPLE 15

4,4,4-Trifluoro-3-hydroxy-3-fluoromethyl-1-(4-phenylsulfonylphenyl)but-1-yne.

To a cooled (−78° C.) solution of 4-phenylsulfonylphenylethyne (1.68 g) in anhydrous tetrahydrofuran (70 mL) was added n-butyl lithium (3.06 mL of a 2.5 M solution in hexanes). The solution was stirred for 15 minutes at −78° C. before 1,1,1,3-tetrafluoroacetone (2.96 mL of a 40% diethyl ether solution) was added. The reaction mixture was kept at −78° C. for five minutes before quenching with 2N hydrochloric acid. Diethyl ether was added and the aqueous layer extracted further with diethyl ether. The combined organic layers were dried, evaporated and the product purified by chromatography, with diethyl ether:chloroform (1:9) as eluent. This yielded the title compound as a white solid (1.64 g) mp 119–120.8; (300 MHz) (CDCl$_3$): 3.77 (s,1, OH), 4.55–4.79 (m,2, CH$_2$F), 7.48–7.61 (m,5, Ar), 7.86–7.94 (m,4, Ar); MS: m/z=373 (M+1). Analysis for C$_{17}$H$_{12}$F$_4$O$_3$S: Calculated: C, 54.84; H, 3.25; Found: C, 54.70; H, 3.37.

EXAMPLE 16

4,4,4-Trifluoro-3-hydroxy-3-methyl-1-(4-[2-pyridylcarbonyl]phenyl)but-1-yne.

To 150 mL tetrahydrofuran was added diisopropylamine (2.4 g), and the mixture was then cooled to −78° C. n-Butyl-lithium was added (8.1 mL, 2.5 molar solution in hexanes). To this mixture was added a solution which had been prepared by dissolving 4-(2-pyridylcarbonyl) phenyl ethyne (3.5 g) in a few mL tetrahydrofuran. The mixture was allowed to stir for 25 minutes. 1,1,1-trifluoroacetone (4.76 g) was added in one portion and the mixture was stirred for 15 minutes. The reaction mixture was then poured into 30 mL aqueous saturated NH$_4$Cl. The ensuing mixture was extracted with 3×300 mL diethyl ether. The organic layers were combined, dried over MgSO$_4$, filtered and evaporated to dryness. The oily residue was chromatographed on silica gel eluting with 80/20 hexane/ethyl acetate. The appropriate fractions were combined and evaporated to dryness. The remaining solid was recrystallized from diethyl ether-hexanes to yield 60 mg of the title compound; mp 116°–118° C.; (300 MHz, (CDCl$_3$): 1.74 (s,3, methyl), 2.79 (s,1, OH), 7.49–7.53 (m,2, aromatic), 7.54–7.58 (d,2, aromatic), 7.89–7.95 (t,1, aromatic), 8.06–8.09 (d,2, aromatic), 8.71–8.73 (d,1, aromatic); Analysis for C$_{17}$H$_{12}$F$_3$O$_2$N: Calculated: C, 63.95; H, 3.79; N, 4.39; Found: C, 63.96; H, 3.97; N, 4.38.

a. To a stirred solution of 1,4-dibromobenzene (70 g) in diethyl ether (200 mL) was added magnesium turnings (8.66 g) at ambient temperature under an N$_2$ atmosphere. After 15 minutes the mixture began to reflux. The reaction mixture was stirred for 5 hours. Stirring was then ceased and after some solids settled to the bottom, the solution was transferred via a cannula into a stirred mixture of 2-cyanopyridine (34.32 g) in diethyl ether (100 mL) at 0° C. The mixture was stired overnight. The mixture was then cooled to 0° C. and 200 mL aqueous 4N HCl was added. The layers were separated. The ether layer was extracted 2×150 mL 4N HCl. The acidic layers were combined and basified with sodium carbonate. The resultant mixture was extracted with 3×300 mL ether. The ether layers were combined, dried over MgSO04, filtered and concentrated by evaporation to afford 44 g of crude material. This was stored at −15° C. overnight and was then distilled at 50 millitorr at 130° C., and redistilled to yield 24.74 g of 4-[2-pyridylcarbonyl]bromobenzene as a white solid. (300 MHz, DMSO): 7.67–7.72 (m,1, aromatic), 7.75–7.79 (d,2, aromatic), 7.91–7.96 (d,2, aromatic), 8.01–8.12 (m,2, aromatic), 8.72–8.74 (d,1, aromatic); MS: (CI) 264 (M+1).

The remaining starting material was prepared as follows:

b. The product of Step 1 (14.12 g) and diethylamine (400 mL) were stirred in a flask. (Trimethylsilyl) acetylene (6.35 g) was added followed by triphenylphosphine palladium chloride (3 g), and the Copper (1) iodide (400 mg) at ambient temperature. The mixture was stirred for 1.5 hours after which time the diethylamine was removed by evaporation and water (500 mL) and chloroform (500 mL) were added to the remaining black residue. The organic layer was separated and the aqueous layer was extracted with 2×500 mL chloroform. All of the organic layers were combined, dried over MgSO$_4$, filtered, and concentrated in vacuo. The remaining black residue was passed through a plug of silica gel (80%. Hexane, 20% Ethyl Acetate). The fractions containing UV active material were combined and the solvent removed by evaporation. The residue was dissolved in methanol (100 mL) and aqueous KOH was added (50 mL, 1N) at ambient temperature. The mixture was stirred for 20 minutes after which time it was poured into 400 mL pH 7.00 buffer. The mixture was extracted with chloroform (3×250 mL). The organic layers were combined, dried over MgSO$_4$, filtered and the solvent was removed by evaporation. The black residue was chromatographed (80% Hexane, 20% Ethyl Acetate). The appropriate fractions were combined and evaporated to dryness. The resultant dark brown solid was dissolved in ether (400 mL), activated charcoal added and the mixture was heated to reflux and filtered hot. The filtrate was stripped to dryness by evaporation to yield 8.5 g of a beige solid. 76% yield. MS: (CI) 208 (Mr). (300 MHz, CDCl$_3$: 3.25 (s,1, acetylenic), 7.26–7.53 (m,2, aromatic), 7.58–7.61 (d,2, aromatic), 7.89–7.94 (m,1, aromatic) 8.04–8.08 (d,2, aromatic) 6.71–8.77 (d, 1, aromatic).

EXAMPLE 17

The following illustrate representative pharmaceutical dosage forms containing a compound of formula I, for example as illustrated in any of the previous Examples, (hereafter referred to as "compound X"), for therapeutic or prophylactic use in humans:

|  | mg/tablet |
|---|---|
| (a) Tablet | |
| Compound X | 50.0 |
| Mannitol, USP | 223.75 |
| Croscarmellose sodium | 6.0 |
| Maize starch | 15.0 |
| Hydroxypropylmethylcellulose (HPMC), USP | 2.25 |
| Magnesium stearate | 3.0 |
| (b) Capsule | |
| Compound X | 10.0 |
| Mannitol, USP | 488.5 |
| Croscarmellose sodium | 15.0 |
| Magnesium stearate | 1.5 |

The above formulations may be obtained by conventional procedures well known in the pharmaceutical art. The tablets may be enteric coated by conventional means, for example to provide a coating of cellulose acetate phthalate.

FORMULAE

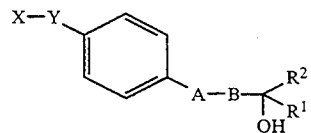

I

-continued
FORMULAE
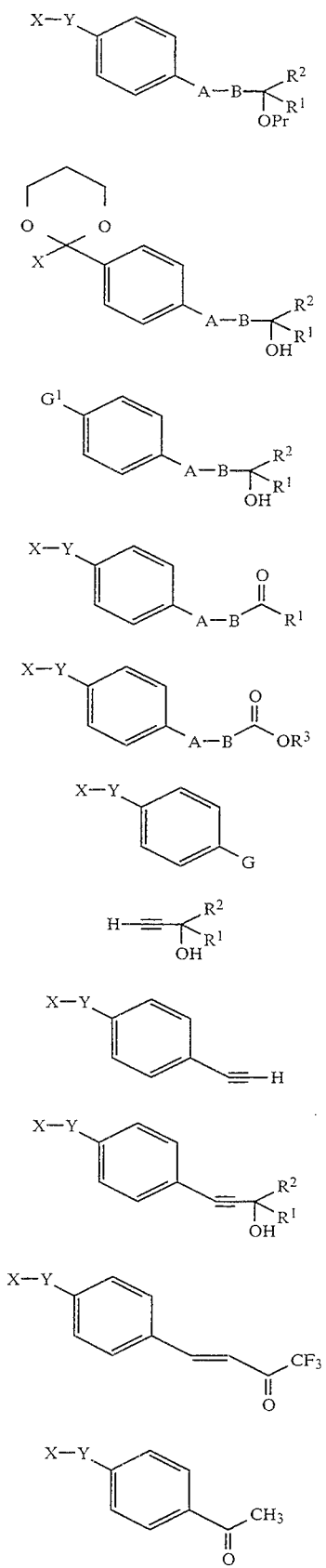
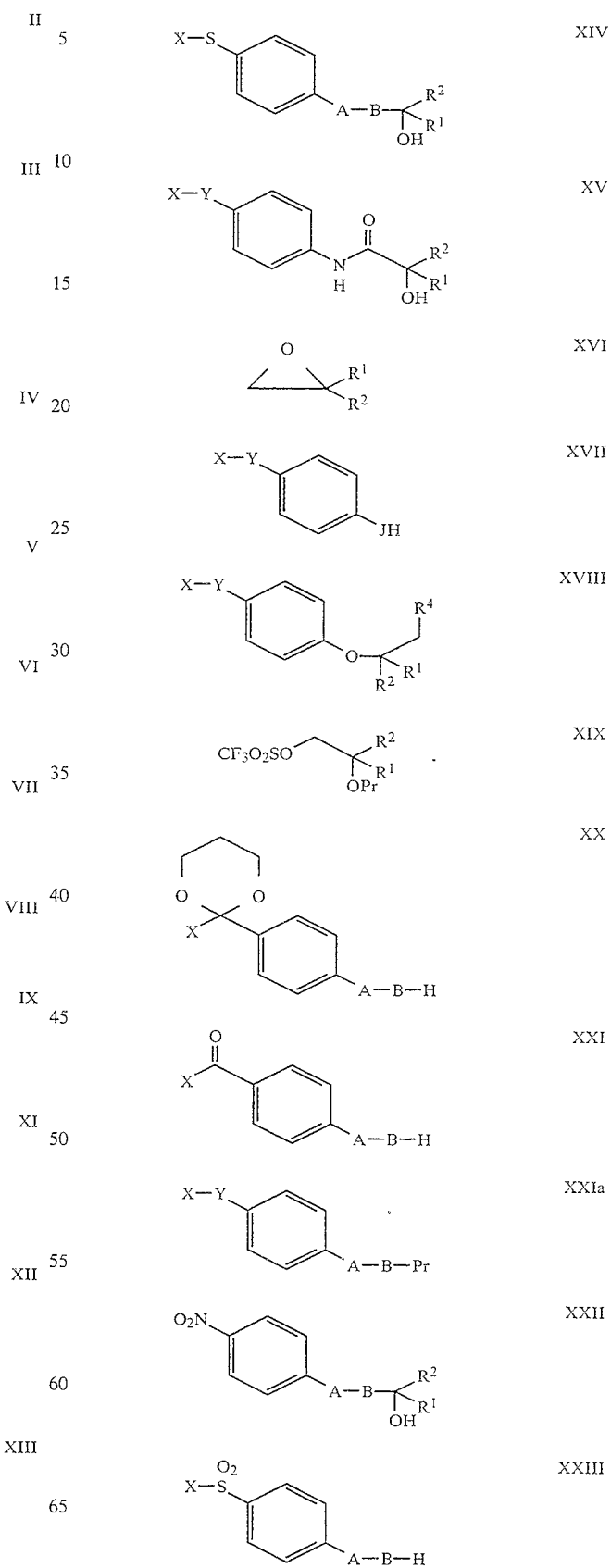

-continued
FORMULAE

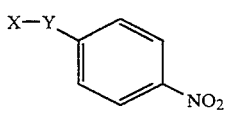 XXIV

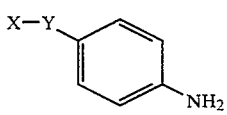 XXV

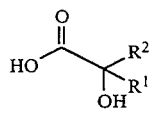 XXVI

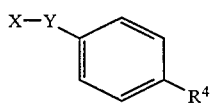 XXVII

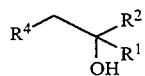 XXVIII

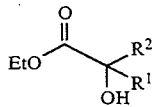 XXIX

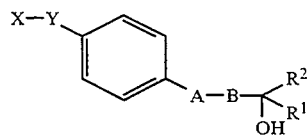 XXX

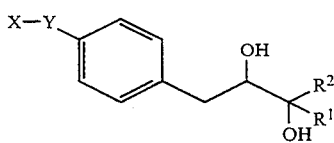 XXXI

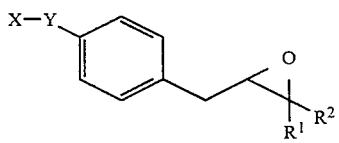 XXXII

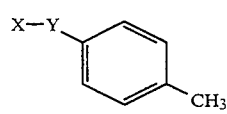 XXXIII

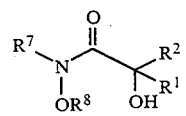 XXXIV

-continued
FORMULAE

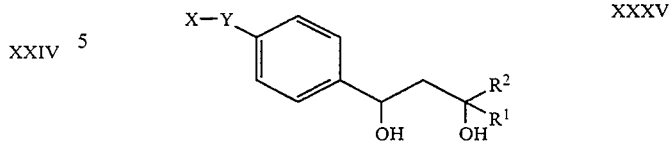 XXXV

We claim:
1. A method for the treatment of urinary incontinence, comprising administering to a mammal in need of such treatment an effective amount of a compound of formula I:

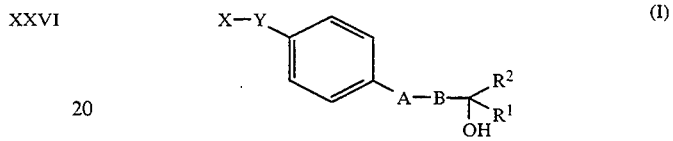 (I)

wherein:
X is selected from
(a) phenyl which may bear 0–2 substituents selected from fluoro, chloro, and hydroxy,
(b) 2-pyridyl, 3-pyridyl, 4-pyridyl, and 2-pyrimidinyl;
Y is selected from sulfonyl or carbonyl;
A–B is selected from OCH$_2$, SCH$_2$, NHCH$_2$, trans-vinylene, and ethynylene;
R$^1$ and R$^2$ are independently selected from the group consisting of methyl, monofluoromethyl, difluromethyl, trifluoromethyl, ethyl and pentafluoroethyl, provided that at least one of R$^1$ and R$^2$ is fluorine-bearing; or a pharmaceutically acceptable in vivo hydrolyzable ester or a pharmaceutically acceptable salt thereof.

2. A method as claimed in claim 1, wherein said compound is:
4,4,4-trifluoro-3-hydroxy-3-methyl-1-(4-phenylsulfonylphenyl)-trans-but-1-ene;
(S)-(—)-4,4,4-trifluoro-3-hydroxy-3-methyl-1-(4-phenylsulfonylphenyl)-trans-but-1-ene;
4,4,4-trifluoro-3-hydroxy-3-methyl-1-(4-phenylsulfonylphenyl)-but-1-yne;
4,4-difluoro-3-difluoromethyl-3-hydroxy-1-(4-phenylsulfonylphenyl)-trans-but-1-ene; or
4,4-difluoro-3-difluoromethyl-3-hydroxy-1-(4-phenylsulfonylphenyl)-but-1-yne; or
a pharmaceutically acceptable in vivo hydrolyzable ester or a pharmaceutically acceptable salt thereof.

3. A method of treatment according to claim 1, wherein R$^1$ and R$^2$ are each difluoromethyl or R$^2$ is trifluoromethyl and R$^1$ is methyl or monofluoromethyl.

4. A method of treatment according to claim 1, wherein X is selected from phenyl, 2-, 3-, and 4-hydroxyphenyl, 2-, 3-, and 4-fluorophenyl, 2-, 3- and 4-chlorophenyl, 2,4-difluorophenyl, 2,3-difluorophenyl, 3,5-difluorophenyl, 2,4-chlorophenyl, 2,3-chlorophenyl, 3,5-dichlorophenyl, 2,4-dihydroxyphenyl, 2,3-dihydroxyphenyl, and 3,5-dihydroxyphenyl.

5. A method of treatment according to claim 1, wherein X is selected from phenyl, 2- and 3-hydroxyphenyl, 2- and 3-fluorophenyl, and 2- and 3-chlorophenyl.

6. A method of treatment according to claim 1, wherein X is selected from phenyl, 2-pyridyl and 4-pyridyl.

7. A method of treatment according to claim 1, wherein A–B is OCH$_2$, trans-vinylene or ethynylene.

* * * * *